United States Patent
Chen et al.

(10) Patent No.: US 8,497,342 B2
(45) Date of Patent: *Jul. 30, 2013

(54) LIQUID CRYSTAL BLOCK COPOLYMER AND METHODS OF MAKING AND USING THE SAME

(75) Inventors: John J. Chen, Plymouth, MN (US); Daniel J. Horn, Shoreview, MN (US); Zhikuan Lu, Hudson, OH (US); Dong Zhang, Uniontown, OH (US); Jiaokai Jing, Uniontown, OH (US); Frank W. Harris, Boca Raton, FL (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/450,677

(22) Filed: Apr. 19, 2012

(65) Prior Publication Data

US 2012/0309901 A1    Dec. 6, 2012

Related U.S. Application Data

(60) Provisional application No. 61/492,978, filed on Jun. 3, 2011.

(51) Int. Cl.
*C08G 64/00* (2006.01)
*C08G 63/02* (2006.01)

(52) U.S. Cl.
USPC .......................... 528/184; 528/190; 528/193

(58) Field of Classification Search
USPC ........................................ 528/184, 190, 193
See application file for complete search history.

(56) References Cited

U.S. PATENT DOCUMENTS

| | | | |
|---|---|---|---|
| 4,490,421 A | 12/1984 | Levy | |
| 5,156,785 A | 10/1992 | Zdrahala | |
| 5,248,305 A | 9/1993 | Zdrahala | |
| 6,024,722 A | 2/2000 | Rau et al. | |
| 6,242,063 B1 | 6/2001 | Ferrera et al. | |
| 6,284,333 B1 | 9/2001 | Wang et al. | |
| 6,325,780 B1 | 12/2001 | Schaible et al. | |
| 6,443,925 B1 | 9/2002 | Schaible et al. | |
| 6,596,219 B2 | 7/2003 | Schaible et al. | |
| 6,730,377 B2 | 5/2004 | Wang | |
| 6,905,743 B1 | 6/2005 | Chen et al. | |
| 6,977,103 B2 | 12/2005 | Chen et al. | |
| 7,582,078 B2 * | 9/2009 | Chen et al. | 604/524 |
| 7,662,129 B2 * | 2/2010 | Chen | 604/96.01 |
| 7,857,785 B2 * | 12/2010 | Chen | 604/96.01 |
| 7,914,484 B2 * | 3/2011 | Yokoyama | 604/83 |
| 8,187,492 B2 * | 5/2012 | Chen | 252/299.01 |
| 2007/0142772 A1 | 6/2007 | Deshmukh et al. | |
| 2010/0016941 A1 | 1/2010 | Chen et al. | |

FOREIGN PATENT DOCUMENTS

WO    2008045166    4/2008

OTHER PUBLICATIONS

Priority U.S. Appl. No. 61/492978, filed Jun. 3, 2011; Inventors: Chen et al.

Moer et al., "Stenting in Small Coronary Arteries (SISCA) Trial, A Randomized Comparison Between Balloon Angioplasty and the Heparin-Coated beStent," Journal of the American College of Cardiology, vol. 38, No. 6, 2001, pp. 1598-1603.

* cited by examiner

*Primary Examiner* — Terressa Boykin
(74) *Attorney, Agent, or Firm* — Vidas, Arrett & Steinkraus, P.A.

(57) ABSTRACT

A liquid crystal block copolymer comprising at least one liquid crystal polymer block comprising a polymer of diethylene glycol bis(4-hydroxybenzoate) and diphenyl 2,6-naphthalene dicarboxylate and at least one non-liquid crystal polymer block.

20 Claims, No Drawings

LIQUID CRYSTAL BLOCK COPOLYMER AND METHODS OF MAKING AND USING THE SAME

CROSS-REFERENCE TO RELATED APPLICATIONS

This application claims priority to U.S. Patent Provisional Application No. 61/492,978 filed Jun. 3, 2011, the entire contents of which are hereby incorporated herein by reference.

BACKGROUND OF THE INVENTION

The present invention relates to liquid crystal block copolymers and to methods of making and using the same.

It is known to use liquid crystal polymers (LCPs) in combination with thermoplastic polymers, i.e. matrix polymers, for use in the manufacture of insertable and/or implantable medical devices such as catheter assemblies and components thereof such as inflatable medical balloons which can be disposed at the distal end of a balloon catheter assembly. For example, see commonly assigned U.S. Pat. Nos. 6,977,103, 6,905,743, 6,730,377 and 6,284,333. See also U.S. Pat. Nos. 6,596,219, 6,443,925 and 6,325,780 to Schaible.

Liquid crystal polymers are known to phase separate from commonly used thermoplastic polymers into multiphase polymer compositions. For example, see U.S. Pat. Nos. 5,248,305 and 5,156,785 to Zdrahala.

Compatibilized blends of LCP and thermoplastic polymers have been found suitable for use as medical device balloon materials. See for example commonly assigned U.S. Pat. No. 6,242,063.

Liquid crystal block copolymers having a non-liquid crystal polymer block that is compatible with commonly employed thermoplastic materials are disclosed in commonly assigned U.S. Pat. Nos. 7,582,078, 7,662,129, 7,857,785 and US Patent Publication No. 2010/0016941 and U.S. patent application Ser. No. 12/974,467.

There continues to be a need for liquid crystal polymers which have increased compatibility with other polymer materials which can be employed in the formation of medical devices, particularly in the manufacture of catheter assemblies or components thereof.

SUMMARY OF THE INVENTION

The present invention relates to polymer compositions useful in the formation of medical devices which include at least one liquid crystal block copolymer having at least one A block and at least one B block.

In one embodiment, the present invention relates to a liquid crystal block copolymer comprising at least one liquid crystal polymer block comprising a condensation polymer composed of diethylene glycol bis(4-hydroxybenzoate) and diphenyl 2,6-naphthalene dicarboxylate and at least one non-liquid crystal polymer block.

In one embodiment the present invention relates to a medical device, at least a portion of the medical device is formed from a polymer composition comprising at least one liquid crystal polymer block comprising a polymer composed of diethylene glycol bis(4-hydroxybenzoate) and diphenyl 2,6-naphthalenedicarboxylate and at least one non-liquid crystal polymer block.

Methods of making and using the same are also disclosed herein.

These and other aspects, embodiments and advantages of the present disclosure will become immediately apparent to those of ordinary skill in the art upon review of the Detailed Description and Claims to follow.

DETAILED DESCRIPTION OF THE INVENTION

While embodiments of the present disclosure may take many forms, there are described in detail herein specific embodiments of the present disclosure. This description is an exemplification of the principles of the present disclosure and is not intended to limit the disclosure to the particular embodiments illustrated.

The description provided herein is not to be limited in scope by the specific embodiments described which are intended as single illustrations of individual aspects of certain embodiments. The methods, compositions and devices described herein can comprise any feature described herein either alone or in combination with any other feature(s) described herein. Indeed, various modifications, in addition to those shown and described herein, will become apparent to those skilled in the art from the foregoing description and accompanying drawings using no more than routine experimentation. Such modifications and equivalents are intended to fall within the scope of the appended claims.

All publications, patents and patent applications mentioned in this specification are herein incorporated by reference in their entirety into the specification to the same extent as if each individual publication, patent or patent application was specifically and individually indicated to be incorporated herein by reference. Citation or discussion of a reference herein shall not be construed as an admission that such is prior art.

The present invention relates to liquid crystal block copolymers including at least one liquid crystal block that is a polymer composed of diethylene glycol bis(4-hydroxybenzoate) and diphenyl 2,6-naphthalenedicarboxylate and at least one non-liquid crystal polymer block.

In some embodiments, the non-liquid crystal polymer block is a polyamide, i.e. nylon, for example. Any nylon may be employed herein including, but not limited to, nylon 6, nylon 66 and nylon 12.

These nylons may be formed by the condensation of hexanedioic acid and hexamethylenediamine (nylon 6,6), ring opening polymerization of caprolactam (nylon 6) or ring opening polymerization of laurolactam (nylon 12), for example. For nylon 6,6, hexanedioyl dichloride may be used in place of hexanedioic acid.

Nylon 6 (polycaprolactam) is not a condensation polymer, but rather is formed by the ring opening polymerization of caprolactam monomers.

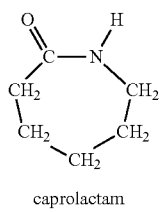

caprolactam

-continued

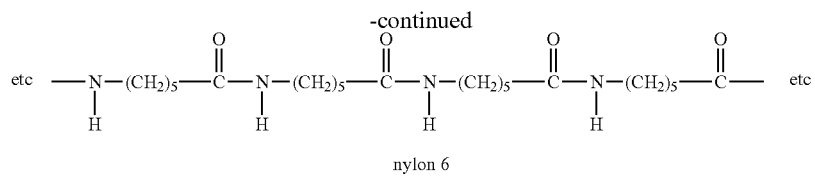

nylon 6

In some embodiments, the non-liquid crystal polymer block is nylon 12. In one particular embodiment, this block is formed by the reaction of dodecanedioic acid and laurolactam.

The liquid crystal polymer block and the non-liquid crystal polymer block can be connected via conventional condensation reactions.

The block copolymers may be of the general formula A-B diblock, A-B-A triblock and B-A-B triblock, polyblock copolymers of the formula $(A-B)_n$ where n is 1 to 20, $A(B-A)_n$ and $B(A-B)_n$ where n is 2 to 20, A-B-A-B-A pentablock, multiblock polymers such as A-B-C, A-C-B or BAC triblock copolymers, $B-(A-B-C)_n$ wherein n is 3 to 20, A-B-C-D multibock copolymers, random block copolymers and alternating random block copolymers, etc.

Furthermore, branched architecture block copolymers including H-type, T-type, stars (including symmetric and heterobranched stars), combs, brushes, dendrons/hyperbranched, etc. may be employed herein.

In some embodiments, the block copolymer may also be of a multiblock variety including C blocks, D blocks, etc. The C block and the D block may be either non-liquid crystal blocks or liquid crystal blocks. For example, in the case of an ABC block copolymer, the A block may be formed of a first mesogenic repeating unit, the B block may be formed of a non-mesogenic repeating unit, and the C block may be formed of a second mesogenic repeating unit different that the first mesogenic repeating unit or the B block is formed from the mesogenic repeating unit and the A and C blocks are formed of non-mesogenic repeating units and the A block and C block are different from one another. See, for example, commonly assigned U.S. Pat. Nos. 7,582,078, 7,662,129, 7,857,785 and US Patent Publication No. 2010/0016941 and U.S. patent application Ser. No. 12/974,467, each of which is incorporated by reference herein in its entirety.

In some embodiments, the block copolymer is a B-A-B block copolymer. Suitably, the A block is the liquid crystal polymer block and the B block is the non-liquid crystal polymer block.

The liquid crystal block copolymer suitably comprises about 50% to about 95% by weight of the A block and about 50% to about 5% by weight of the B block accordingly.

In some embodiments, the liquid crystal block copolymer comprises about 60% to about 90% by weight of the liquid crystal polymer block and about 40% to about 10% by weight of the non-liquid crystal polymer block accordingly.

The relative number average molecular weight of the liquid crystal block copolymer may be from about 10,000 grams/mole to about 100,000 grams/mole, more suitably about 15,000 grams/mole to about 50,000 grams/mole. In one embodiment, the molecular weight was found to be about 20,000 grams/mole.

The A block may have anywhere from about 20 to about 200 repeating units, and more suitably about 20 to about 50 repeating units, and the B block may have anywhere from about 2 to about 50 repeating units, and suitably about 2 to about 25 repeating units.

In specific embodiments, a B-A-B block copolymer wherein the A block is the liquid crystal polymer block and the B block is the non-liquid crystal polymer block is formed.

In a specific embodiment, described in thorough detail in example 1 below, a liquid crystal block copolymer is prepared having a liquid crystal polymer block formed from a diethylene glycol bis(4-hydroxybenzoate) monomer and a diphenyl naphthalene 2,6-dicarboxylate monomer and a non-liquid crystal block formed primarily of nylon 12 which is the reaction product of dodecandioic acid and laurolactam.

The architecture is suitably a B-A-B block copolymer wherein the A block is the liquid crystal polymer of diethylene glycol bis(4-hydroxybenzoate) and diphenyl naphthalene 2,6-dicarboxylate and the B block is the non-liquid crystal polymer block of nylon 12.

In one embodiment, the mole ratio of diethylene glycol bis(4-hydroxybenzoate) and diphenyl naphthalene 2,6-dicarboxylate is about 1:1.

The block copolymer exhibits a low melting points of about 275° C. or less, suitably about 250° C. or less, even more suitably about 150° C. to about 200° C. which makes them easy to process and more thermally compatible with other conventional plastics. The liquid crystal block copolymer further exhibits a high modulus or stiffness similar to that of conventional liquid crystal polymers or polyimides, high tensile strength superior to that of nylon 12 alone, and it is not brittle.

The block copolymer disclosed herein also is compatible with typical materials used in catheter devices and can thus be readily melt blended or admixed therewith.

Examples of thermoplastic polymers which may be employed in a blend with the liquid crystal block copolymer disclosed herein include, but are not limited to, polyamides, polyesters, polyethers, polyolefins, polyimides, block copolymers comprising at least one polyolefin, polyester, polyether, polyamide, and/or polyimide segment, silicones, and mixtures thereof and mixtures thereof.

A specific example of a class of thermoplastic polymer materials that finds utility in a melt blend with the liquid crystal polymer disclosed herein is the amide family of materials such as polyether-block-amides for example, as well as nylon 12, amorphous nylons, etc. These materials exhibit excellent compatibility with the liquid crystal block copolymer because of the similarity to the amide block.

Of course, more than one liquid crystal polymer and non-liquid crystal polymer may also be included in the polymer composition.

The amount of LCP block copolymer employed may be from about 5% to about 75% and more suitably about 5% to about 50% and even more suitably about 10% to about 30% and about 25% to about 95%, more suitably about 50% to about 95% and even more suitably about 70% to about 90% of a non-liquid crystal polymer.

Most suitably, the polymer composition includes about 5% to about 30% of the liquid crystal block copolymer and about 70% to about 95% of the non-liquid crystal polymer, but is not limited as such.

EXAMPLE 1

A liquid crystal copolymer block was prepared using diethylene glycol bis(4-hydroxybenzoate) and diphenyl 2,6-naphthalenedicarboxylate using the following procedure.

In a first step, diethylene glycol bis(4-hydroxybenzoate) (monomer component 1) was prepared according to the following chemical reaction:

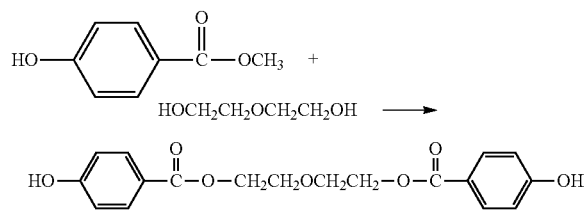

The reaction of methyl 4-hydroxy benzoate (152.2 g) and diethylene glycol (42.4 g) was conducted at 170° C. for about 24 hrs under nitrogen gas and in the presence of catalytic amount of n-butyl titanate. The resulting product was purified and dried. The purified monomer (80 g) was characterized by thin layer chromatography (TLC) and proton nuclear magnetic resonance (NMR).

In a second step, diphenyl 2,6-naphthalene-dicarboxylate (monomer component 2) was prepared according to the following chemical reaction:

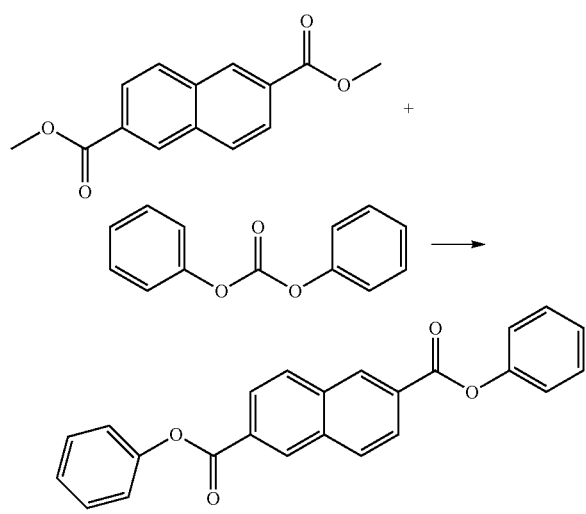

Dimethyl naphthalene-2,6-dicarboylate (171 g), diphenyl carbonate (180 g) and titanium butoxide (1 mL) were placed in a dry 1000 ml three neck round-bottom flask equipped with a mechanical stirring, nitrogen inlet and a distillation short path. The reaction mixture was heated to 240° C. Dimethyl carbonate started distilling out after about 1 hour with continued stirring and a flow of nitrogen. The reaction temperature was gradually increased to 260° C. over a 3 hour period. The reaction was continued until all the starting dimethyl ester was converted to the diphenyl ester as indicated by TLC. The resulting product was purified and dried. The final product (189 g) was characterized by proton NMR.

In a third step, the liquid crystal polymer (LCP) block was prepared. A 1:0.97 mole ratio of diethylene glycol bis(4-hydroxybenzoate) and diphenyl naphthalene 2,6-dicarboxylate was used in the polymerization to ensure hydroxyl chain ends in the finished liquid crystal polymer. Diethylene glycol bis(4-hydroxybenzoate) (135.07 g), diphenyl naphthalene-2,6-dicarboylate (139.36 g) and antimony oxide (200 mg) were placed in a 500 mL three-neck round-bottom flask equipped with an argon inlet, a mechanical stirring and a distillation short path. Air was evacuated from the system and argon was refilled. The reaction system was kept under argon atmosphere with a slow steam of argon. The polymerization was conducted at 280° C. The polymerization was conducted for approximately 10 hours with a constant slow flow of argon to remove the evolving phenol through a distillation short path. After the phenol distillation was nearly complete, vacuum was applied and the reaction continued until a shining liquid crystal phase appeared. No more phenol evolved from the reaction. This process took about 10 hours.

The final liquid crystal polymer block was extracted in a Soxhlet apparatus with chlorobenzene for 24 hour. Other solvents such as toluene or xylene, for example, may also be used for extraction purpose. The final product was characterized by GPC (gel permeation chromatography) for molecular weight. The product had a relative weight average molecular weight of about 45,000 grams/mole.

In a fourth step, the nylon 12 oligomer block was prepared. Dodecanedioic acid and laurolactam were reacted as follows:

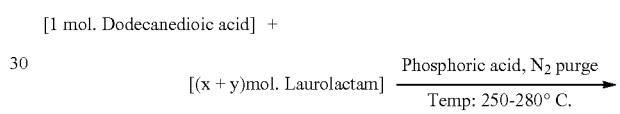

The nylon 12 oligomer block is represented by the following chemical formula:

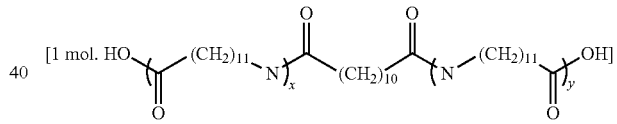

This nylon 12 oligomer block was actually prepared in two separate processes. The first was to make Nylon 12 oligomer with acid chain ends per synthetic scheme above. The resulting product had a relative weight average molecular weight of about 2,500 grams/mole as characterized by GPC.

The second process was to convert the acid chain ends to phenyl ester chain ends for reactivity enhancement in block copolymer polymerization. In this process, the nylon 12 oligomer product (71 g) was reacted with diphenyl carbonate (90 g) in the presence of 4-dimethylpyridine (120 mg) at 180° C. under nitrogen. The gas evolution stopped as the mixture became a completely homogeneous melting solution. This chain end exchange reaction was continued for another 10 minutes after the mixture become a homogeneous melt solution. The product was quickly precipitated into toluene solution with rapid stirring. The toluene solution was heated to boiling and the resulting solid product was filtered. The product was further purified with toluene in a Soxhlet apparatus for 8 hours. The final product was characterized by GPC to confirm molecular weight retention during the processes.

In a fifth step, the Liquid Crystal block copolymer was prepared.

The LCP (55.0 g) and functionalized nylon-12 oligomer block (16.4 g) were added into a reactor with an antimony oxide (30 mg) catalyst at a 1:2 mole ratio. The reaction was carried out under argon gas at 215 to 225° C. with a stirring mechanism. After the contents in the reactor melted, agitation was applied and the reaction was continued for 20 minutes. A vacuum was gradually to reach a high vacuum for over 20 minutes. After about 1 to 6 hours, the product was pulled out as fibers.

The relative weight average molecular weight of the liquid crystal block copolymer was about 81,000 grams/mole when using the same column and solvents as used for the liquid crystal polymer block and nylon oligomer block.

This liquid crystal block copolymer exhibited a melting temperature of about 180° C.

The liquid crystal block copolymer was melt spun into fiber at 190° C. and the fiber tensile strength was about 15,000 psi with elongation at yield of about 4%.

The liquid crystal block copolymers disclosed herein and any blends thereof may be employed in the manufacture of any medical device or component thereof which is suitably formed from polymer compositions, for example, catheter assemblies and components thereof, including, for example, shafts, tips, manifolds and expandable medical balloons.

The present invention finds utility in the manufacture of expandable medical balloons, particularly those employed in the cardiovascular system wherein the balloon size is very small.

Balloon formation is known in the art. In some processes, a tube of polymer material is extruded and then expanded radially and axially. Balloon formation is described in U.S. Pat. No. 4,490,421 and in commonly assigned U.S. Pat. Nos. 6,024,722, both of which are incorporated by reference herein in their entirety. Of course, other processes are known and may be employed in the present invention.

The above disclosure is intended to be illustrative and not exhaustive. This description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

The invention claimed is:

1. A liquid crystal block copolymer comprising at least one liquid crystal polymer block comprising a polymer of diethylene glycol bis(4-hydroxybenzoate) and diphenyl-2,6-naphthalenedicarboxylate and at least one non-liquid crystal polymer block.

2. The liquid crystal block copolymer of claim 1 wherein said mole ratio of diethylene glycol bis(4-hydroxybenzoate) to diphenyl 2-6-naphthalene dicarboxylate in the liquid crystal polymer block is about 1:1.

3. The liquid crystal block copolymer of claim 1 wherein the non-liquid crystal polymer block is polyamide.

4. The liquid crystal block copolymer of claim 1 wherein the non-liquid crystal polymer block comprises nylon-12.

5. The liquid crystal block copolymer of claim 1 selected from the group consisting of at least one member selected from the group consisting of an A-B diblock copolymer, an $(A-B)_n$ block copolymer wherein n is 1 to 20, an $A(B-A)_n$ block copolymer where n is 2 to 20, a $B(A-B)_n$ block copolymer wherein n is 2 to 20, an A-B-A block copolymer, a B-A-B block copolymer, an A-B-A-B-A block copolymer, a B-A-B-A-B block copolymer, a multiblock copolymer, a linear tetrablock copolymer, a random block copolymer and a random alternating block copolymer, a radial star block copolymer, an H-type branched block copolymer, a T-type branched block copolymer, a comb, a brush and a dendrons.

6. The liquid crystal block copolymer of claim 5 wherein the A block is the liquid crystal polymer block and the B block is the non-liquid crystal polymer block.

7. The liquid crystal block copolymer of claim 1, the liquid crystal block copolymer is a mixture of B-A-B and B-A-B-A-B liquid crystal block copolymer wherein the A block is the liquid crystal polymer block and the B block is the non-liquid crystal polymer block.

8. The liquid crystal block copolymer of claim 7, the liquid crystal block copolymer comprises about 50% to about 95% by weight of said liquid crystal polymer block and about 5% to about 50% by weight of said non-liquid crystal polymer block.

9. The liquid crystal block copolymer of claim 7, the liquid crystal block copolymer comprises about 60% to about 90% by weight of said liquid crystal polymer block and about 10% to about 40% by weight of said non-liquid crystal polymer block.

10. The liquid crystal block copolymer of claim 1 in a polymer blend, the polymer blend further comprising at least one non-liquid crystal polymer which is a member selected from the group consisting of polyamides, polyesters, polyethers, polyolefins, polyimides, block copolymers comprising at least one polyolefin, polyester, polyether, polyamide, and/or polyimide segment, silicones, and mixtures thereof and mixtures thereof.

11. The liquid crystal block copolymer of claim 1 in a polymer blend, the polymer blend further comprises at least one polyether-block-amide copolymer.

12. The liquid crystal block copolymer of claim 10 wherein said melt blend comprises about 5% to about 30% of said liquid crystal block copolymer and about 70% to about 95% of said non-liquid crystal polymer.

13. A medical device, at least a portion of said medical device is formed from a polymer composition comprising at least one liquid crystal polymer block comprising a polymer of diethylene glycol bis(4-hydroxybenzoate) and diphenyl 2,6-naphthalenedicarboxylate and at least one non-liquid crystal polymer block.

14. The medical device of claim 13 wherein the non-liquid crystal polymer block is polyamide.

15. The medical device of claim 13 wherein the non-liquid crystal polymer block is nylon-12.

16. The medical device of claim 13 wherein the liquid crystal block copolymer comprises about 50% to about 95% by weight of said liquid crystal polymer block and about 5% to about 50% by weight of said non-liquid crystal polymer block.

17. The medical device of claim 13 wherein the polymer composition further comprises at least one non-liquid crystal polymer which is a member selected from the group consisting of polyamides, polyesters, polyethers, polyolefins, polyimides, block copolymers comprising at least one polyolefin, polyester, polyether, polyamide, and/or polyimide segment, silicones, and mixtures thereof and mixtures thereof.

18. The medical device of claim 13 wherein the polymer composition further comprises a polyether-block-amide copolymer.

19. The medical device of claim 17 wherein the polymer composition comprises about 5% to about 30% of said liquid crystal block copolymer and about 70% to about 95% of said non-liquid crystal polymer.

20. The medical device of claim 13, the medical device is a catheter shaft or expandable medical balloon.

* * * * *